United States Patent
Agostinelli et al.

(10) Patent No.: US 12,290,348 B2
(45) Date of Patent: May 6, 2025

(54) SYSTEMS AND METHODS FOR DETECTING MAGNETIC MARKERS FOR SURGICAL GUIDANCE

(71) Applicant: ENDOMAGNETICS LIMITED, Cambridgeshire (GB)

(72) Inventors: Tiziano Agostinelli, Cambridge (GB); Simon Richard Hattersley, Cambridge (GB)

(73) Assignee: ENDOMAGNETICS LIMITED (GB)

( * ) Notice: Subject to any disclaimer, the term of this patent is extended or adjusted under 35 U.S.C. 154(b) by 107 days.

(21) Appl. No.: 17/926,765

(22) PCT Filed: May 18, 2021

(86) PCT No.: PCT/IB2021/054244
§ 371 (c)(1),
(2) Date: Nov. 21, 2022

(87) PCT Pub. No.: WO2021/250485
PCT Pub. Date: Dec. 16, 2021

(65) Prior Publication Data
US 2023/0200675 A1   Jun. 29, 2023

(30) Foreign Application Priority Data
Jun. 8, 2020   (GB) .................................... 2008600

(51) Int. Cl.
*A61B 5/06*   (2006.01)
*A61B 90/00*   (2016.01)

(52) U.S. Cl.
CPC ................ *A61B 5/06* (2013.01); *A61B 90/39* (2016.02); *A61B 2090/3954* (2016.02)

(58) Field of Classification Search
CPC ........... A61B 5/06; A61B 5/062; A61B 5/064; A61B 90/39; A61B 2090/3954; A61M 25/0127
See application file for complete search history.

(56) References Cited

U.S. PATENT DOCUMENTS 5,801,630 A * 9/1998 Ho ..................... G08B 13/2437
                                                    148/120
6,230,038 B1   5/2001 von Gutfeld et al.
(Continued)

FOREIGN PATENT DOCUMENTS

EP    2967428 B1    5/2019
WO    2019/180580 A1   9/2019

OTHER PUBLICATIONS

PCT International Search Report and PCT Written Opinion for PCT International Application No. PCT/IB2021/054244; mailing date Aug. 12, 2021; (10 pages).

*Primary Examiner* — Steven L Yeninas
(74) *Attorney, Agent, or Firm* — K&L GATES LLP

(57) ABSTRACT

A method for detecting a magnetic marker comprises generating a driving magnetic field comprising first and second frequencies and detecting a response magnetic field comprising first and second response components. The magnetic marker provides a non-linear response to the driving signal. A primary portion of the response components is generated by the magnetic marker, and secondary portion of the response components is generated by a secondary magnetic source. The method comprises determining a driving factor representing a ratio of the frequencies in the driving signal; determining a correction factor corresponding to the secondary portion of the second response component, based on the first response component and the driving factor; determining a detection signal corresponding to the primary portion of the second response component, based on the (Continued)

second response component and the determined correction factor; and generating an output signal based on a strength of the detection signal.

19 Claims, 8 Drawing Sheets

(56) References Cited

U.S. PATENT DOCUMENTS

| | | |
|---|---|---|
| 6,337,627 B1 | 1/2002 | Von Gutfeld et al. |
| 2004/0254453 A1 | 12/2004 | Govari |
| 2019/0209263 A1 | 7/2019 | van der Weide et al. |
| 2019/0223975 A1 | 7/2019 | Agostinelli et al. |

* cited by examiner

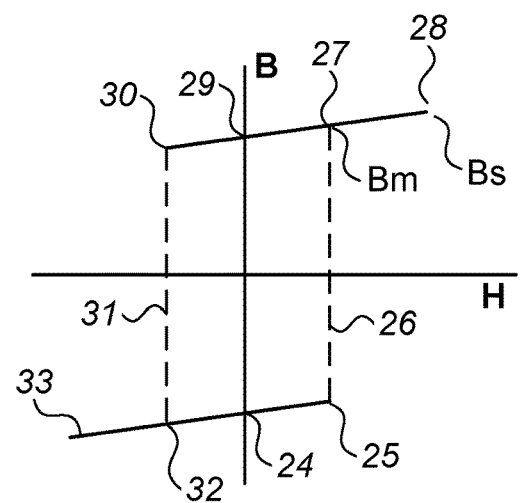
FIG. 5A
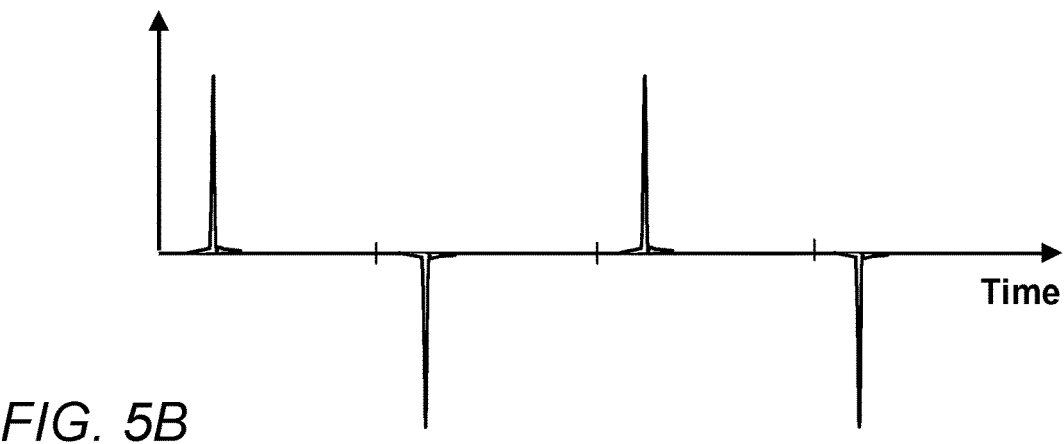
FIG. 5B
FIG. 5C
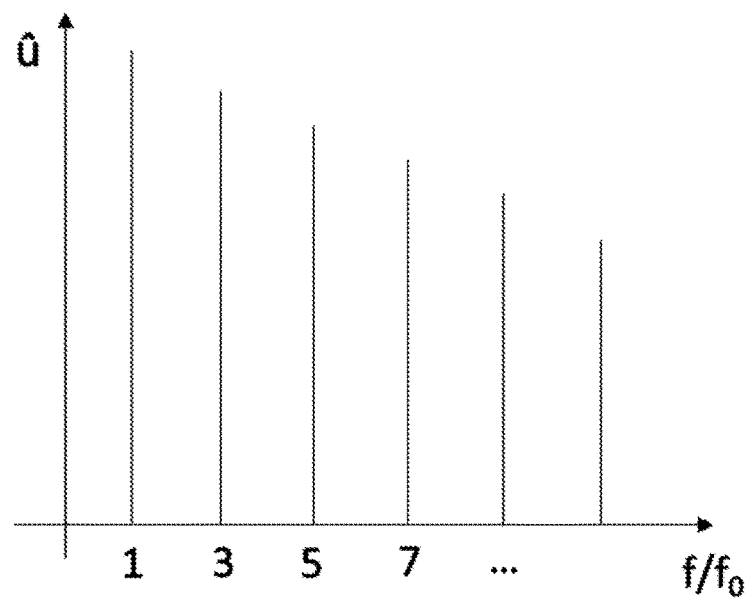

SYSTEMS AND METHODS FOR DETECTING MAGNETIC MARKERS FOR SURGICAL GUIDANCE

CROSS REFERENCE TO RELATED APPLICATIONS

This is the national phase under 35 U.S.C. § 371 of International Application No. PCT/IB2021/054244 filed on May 18, 2021, which claims priority to and the benefit of United Kingdom Application No. 2008600.5 filed on Jun. 8, 2020, the entire disclosures of each of which are incorporated by reference herein.

FIELD OF THE INVENTION

This invention relates in general to the field of surgical guidance, more specifically to systems and methods for detecting markers and tracers that aid in locating a site in the body, for example, a lesion for surgical excision.

BACKGROUND OF THE INVENTION

Markers are used to guide surgeons to a region of interest during a surgical procedure, where the site of interest is not physically visible or palpable, for example a small tumour that needs to be excised. The marker may be placed during a biopsy or other surgical procedure at a site of interest in the body, for example a cancer lesion. Ideally, such a marker will be deployable through a narrow gauge needle. The marker is placed under imaging guidance such as ultrasound or X-ray/mammography. During subsequent surgery, the marker is detected and localised using a handheld probe which provides audible, visual or other feedback to the surgeon to guide the surgery. Typically the marker is excised along with the surrounding tissue.

A marker can also be used to mark a lymph node before a course of neo-adjuvant therapy. In this way a node can be readily identified after the neo-adjuvant therapy for excision, even if fibrosis from the therapy has affected the lymphatics so that conventional lymphatic tracers are not able to flow to the draining lymph nodes.

One such tumour-marking approach is to use a marker containing a radioisotope such as Iodine 90 which can be detected using a handheld gamma detection probe, e.g., a geiger counter. However, use of radioactive materials is closely regulated, making it challenging to set up a radioactive seed programme in all but the largest academic hospital centers.

A further approach is discussed in the Applicant's earlier published patent applications (for example, WO 2011/067576, WO 2014/013235 and WO 2014/140567) and uses magnetic fields and a magnetic marker with high magnetic susceptibility. A handheld probe generates an alternating field which excites a magnetically responsive marker, and detects the responding magnetic field.

Markers that are liquid or liquid-borne may also be used in a surgical procedure, for example in the detection of sentinel lymph nodes for a biopsy. Such markers may be referred to as "tracers". Sentinel lymph node biopsy is an important technique used to stage some cancers, that is to evaluate the spread of certain cancer types, particularly breast cancer. A tracer can be injected near a cancer tumour. The tracer particles are then taken up in the lymphatic system and flow to the draining lymph nodes where they accumulate. The nodes may then located either by visual discoloration of the node or using a handheld probe so that they can be excised for pathological assessment. The nodes identified in this way are called 'sentinel' nodes because they are the ones to which the cancer may spread. The surgical procedure to identify and remove them is known as a sentinel lymph node biopsy procedure.

Typically, the two procedures, excision of the tumour and excision of the lymph nodes happen in the same operation. Thus the tracer and marker can both be present in the breast at the same time.

As above, one approach is to use a liquid marker containing a radioisotope, e.g., a technetium-99m sulfur colloid. The radio-labelled colloid particles accumulate in the draining lymph nodes which can then be identified for excision using a handheld gamma probe (Geiger counter). However, technetium-99m has only a 6 hour half-life and so must be injected close to the time of surgery, thus creating a scheduling challenge. It may also have a complicated supply chain, and may not be available to isolated hospitals. There may also be interruptions in supply if a reactor producing the isotope is out of operation at a given time.

A further approach is to use a suspension of superparamagnetic iron oxide nanoparticles. These particles have no half-life which means that they can be available in any hospital and can be injected a number of days before surgery, making scheduling more convenient.

The nanoparticles can be detected by a magnetic probe such as the handheld probe above. However, such a probe may then respond to both a magnetic marker and an iron oxide nanoparticle suspension. In particular, a portion of the nanoparticle suspension may remain in the region of an injection site near the lesion. It is desirable to carry out a lesion removal procedure and a sentinel lymph node biopsy in a single surgery, however, it has proved problematic to provide a detection system that is able to distinguish the lesion marker from other magnetically responsive materials. This is illustrated in FIG. 1A.

Other magnetically responsive materials include surgical tools made from metal. It is desirable to develop magnetic markers or tracers that can be detected in the presence of metallic tools. This is illustrated in FIG. 1B.

The human body itself has a magnetic response that can interfere with the detection of a magnetic marker because the water that is the main constituent of human tissue can give a diamagnetic response. Typically, a large amount of human tissue is surrounding the injected marker during a localization procedure. A marker that can be accurately localized against the backdrop signal from the human body is therefore advantageous. This is illustrated in FIG. 1C.

Multiple markers may be present at the lesion site. For example, a biopsy marker may have previously been placed to monitor the evolution of the tumoral mass over time by means of mammography or ultrasound scans. It is desirable that a probe adapted for lesion localization during surgery is only sensitive to the marker placed for this purpose. This is illustrated in FIG. 1D.

If a magnetic marker is used to mark a particular lymph node and a magnetic tracer is also used to map and identify other sentinel lymph nodes, then there may be one of more lymph nodes in which there is a magnetic marker and a magnetic tracer. It is advantageous to be able to localize and identify which lymph nodes are marked and which only contain the tracer. It may also be advantageous to be able to quantify the amount of tracer in the node even in the presence of a marker. Thus, there is a need to discriminate between a marker and a tracer within a lymph node. This is illustrated in FIG. 1E.

One proposed solution to the above issues is to use a marker that responds non-linearly to the exciting magnetic field. It is possible to analyse the full harmonic response to discriminate the marker from the tracers, metallic tools, the body or other markers that have a different and typically more linear response at the same field intensities.

Materials with a large Barkhausen discontinuity in the magnetisation curve, or 'Large Barkhausen Jump' (LBJ) materials, undergo a rapid reversal of their magnetic polarization when excited by an external magnetic field whose field strength opposing the instantaneous magnetic polarization of the wire exceeds a predetermined threshold value, also known as a switching field. Thus, the marker exhibits bistable behaviour, reversing between two magnetic polarisation states. Each reversal of magnetisation generates a magnetic pulse with harmonic components. The profile and number of harmonics is measured (out to many tens of harmonics) to identify the marker from other materials.

It has been shown (for example CA3031282A1) that some LBJ materials can exhibit a strong non-linear response even when the marker is shorter than the critical length and/or is excited below the switching field. Markers formed from such materials are known as sub-bistable markers. Other markers with a smaller level or different type of non-linearity in their magnetic response could also be considered for discrimination against more linear secondary signals. For example, the non-linearity could be the result of the inclusion of a non-linear electronic component in the marker, like a diode.

Ideally, an exciting magnetic field generated by the magnetic probe (the drive field) should only include one frequency component at the fundamental frequency. Strong magnetic fields are also desirable to achieve large detection distances. However, it is challenging to produce an alternating magnetic field around the probe with both a high field strength and a pure single-frequency sinusoidal waveform at the desired frequency. When an amplifier is driven with sufficient power to produce a strong field, typically some distortion or impurity is introduced in the sinusoidal waveform, which results in harmonics of the drive frequency being added.

Harmonic components in the drive field may cause a response from any linear tracer or markers at the same harmonic frequencies. This results in interference with the harmonic signal produced by the non-linear marker and can impede its detection and characterization, as shown in FIG. 2.

Low distortion operational amplifiers can provide a harmonic distortion of about −120 dB, where harmonic distortion is a ratio of the rms value of the harmonic of interest ($2^{nd}$, $3^{rd}$, etc) to the rms signal level. However, such low distortion is achieved only at currents of tenths of mA, which are generally too low. Such amplifiers also use resistive loads in general, while magnetic probes typically use inductive loads. Furthermore, the harmonic distortion of operational amplifiers is typically measured by looking at voltages rather than current. However, in this application the relevant Harmonic Distortion is that of the magnetic field, which is generated from a current rather than a voltage. It is therefore not straightforward to produce highly pure drive fields with off-the-shelf electronic components.

A typical optimized harmonic distortion for the drive field in a magnetic probe such as that in WO 2011/067576, WO 2014/013235 or WO 2014/140567 may be in the range of −70 dB to −100 dB at the frequencies of interest. This indicates harmonic components less than 10000-100000 times smaller than the drive signal, and is acceptable for most applications that rely on a linear detection or even for high end audio systems. However, in this application such a level of harmonic distortion in the drive, when reflected by a linear magnetic material near to the probe, may easily be as large as the signal from a non-linear marker at some distance from the probe. Thus, there is a need to provide a system that is able to distinguish a non-linear marker from other magnetically responsive materials even with a non-pure drive field. The present invention aims to address this need.

SUMMARY OF THE INVENTION

According to a first aspect of the present invention, there is provided a method for detecting a marker according to claim 1.

Optional features are as set out in the dependent claims.

BRIEF DESCRIPTION OF THE DRAWINGS

For a better understanding of the present invention and to show more clearly how it may be carried into effect, reference will now be made by way of example only, to the accompanying drawings, in which:

FIG. 5A is a chart showing a magnetisation curve for an exemplary marker;

FIG. 5B is a chart showing a magnetic response in the time domain;

FIG. 5C is a chart showing a magnetic response in the frequency domain;

DETAILED DESCRIPTION OF THE INVENTION

The present invention relates to a detection system and method for characterizing a marker, and more particularly a magnetic marker that can be implanted for marking a target site in the body, and to the detection and localisation of the implanted marker using a handheld probe.

The marker may be implanted in a site requiring marking in the body. This may, for example, be a tumour or other lesion or site of interest in soft tissue. Examples include but are not limited to benign lesions, cancerous lesions and lymph nodes. The marker may be placed in or near a lesion or multiple markers may be placed to mark the margins or perimeter of a surgical site, for example the margins of a tumour or soft tissue sarcoma.

Figure 1A:
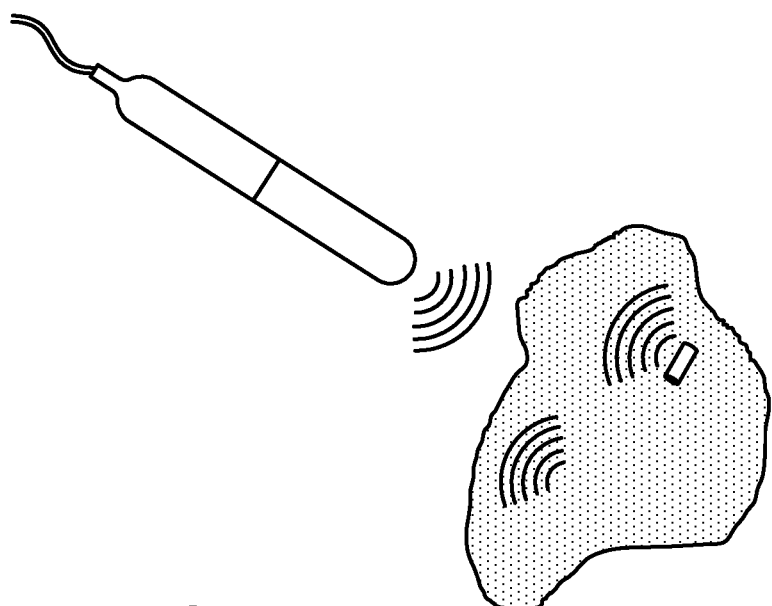
FIGS. 1A to 1E are illustrations indicating usage scenarios for an embodiment.
Figure 1B:
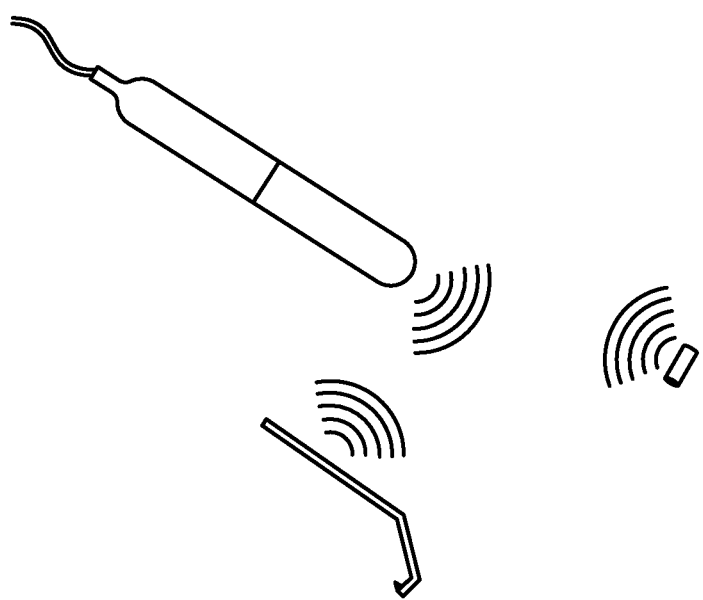
Figure 1C:
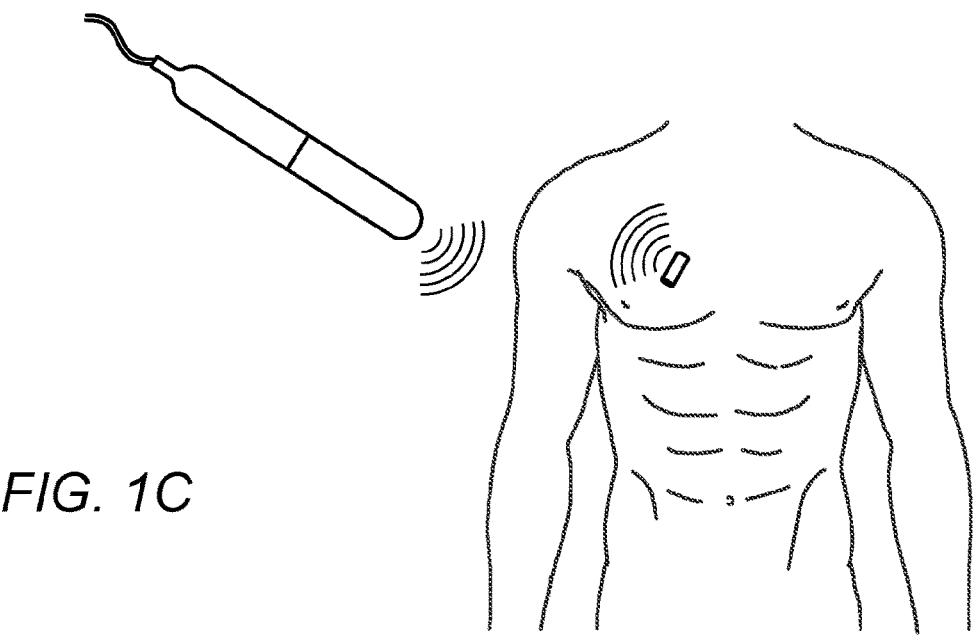
Figure 1D:
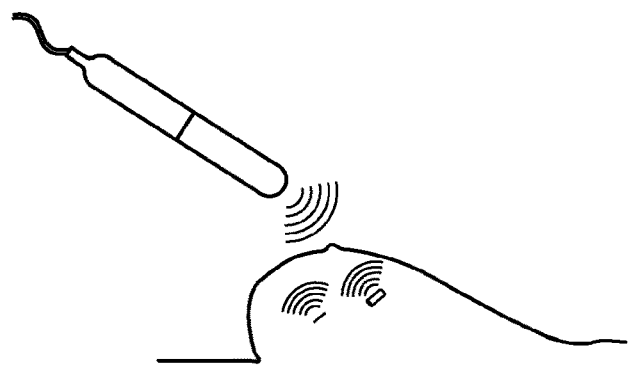
Figure 1E:
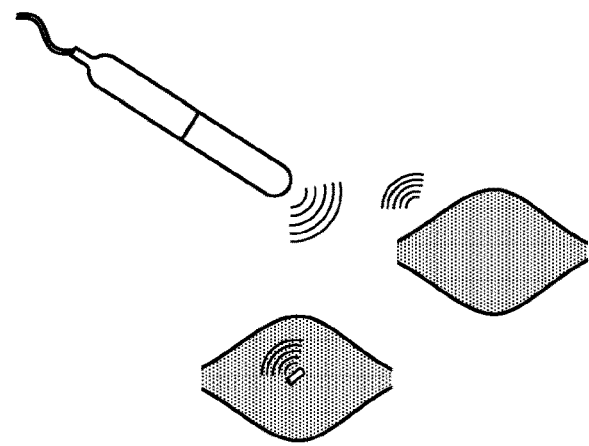
Figure 2:
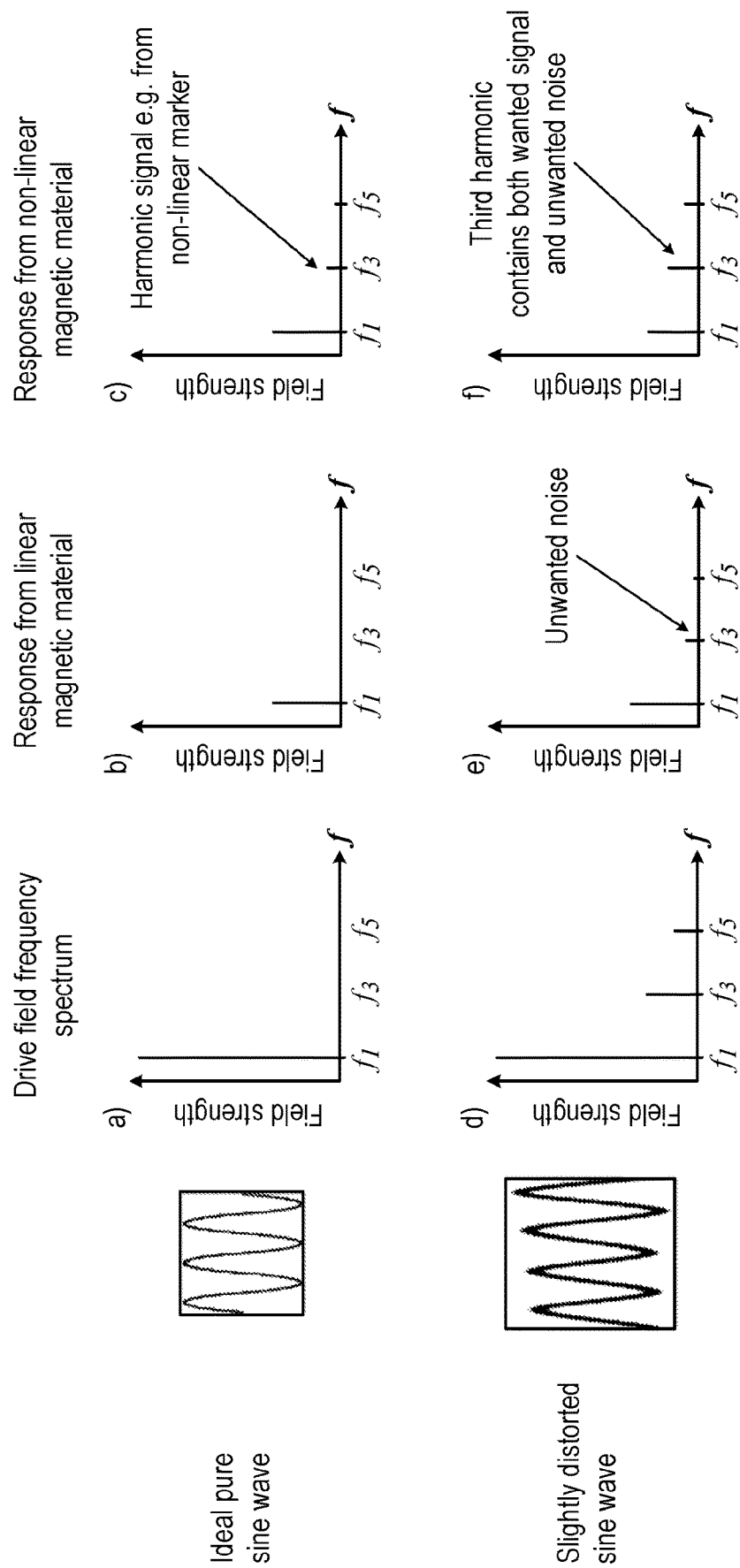
FIG. 2 is a number of charts showing the effect of a harmonic component in the driving field.
Figure 3:
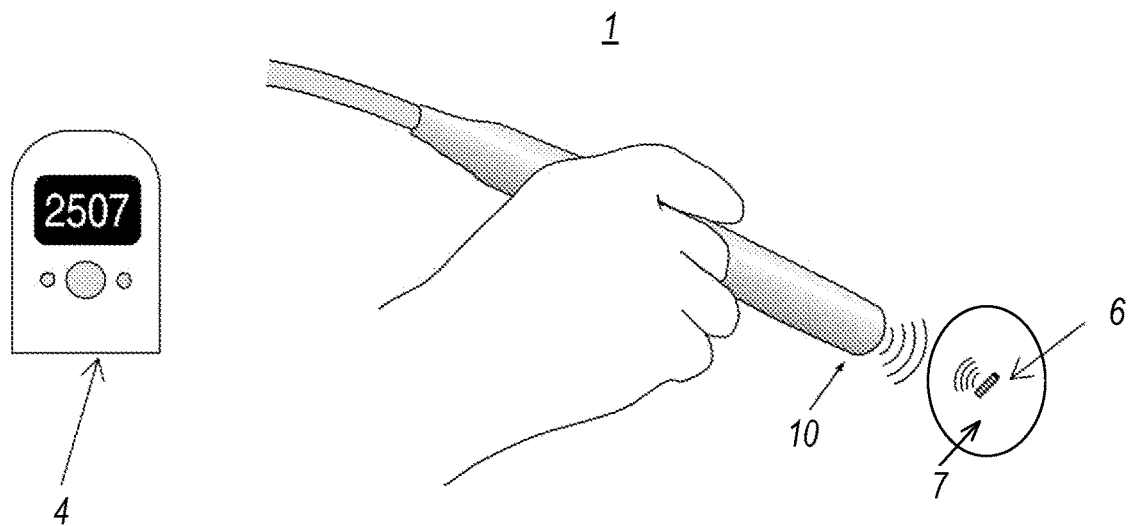
FIG. 3 is a schematic diagram of a magnetic detection system according to an embodiment.

FIG. 2 of the accompanying drawings shows a schematic diagram of an embodiment of a detection system and marker according to the present invention. The detection system 1 comprises a probe 10 connected to a base unit 4. The probe 10 has one or more drive coils that generate an alternating magnetic field to excite a magnetic marker 6. A magnetic tracer 7 may also be present near the marker 6.

The marker 6 comprises at least one piece of magnetically responsive material and may have a non-linear magnetic susceptibility. A magnetisation of the material may respond in a non-linear fashion to an external magnetic field. The material may have a large Barkhausen discontinuity in its magnetisation curve, and may be known as a large Barkhausen jump material, a LBJ material, a bistable switching material or a material with large non-linearities in its magnetisation curve. For example, when the LBJ material is exposed to an external magnetic field whose field strength opposing the instantaneous magnetic polarization of said length of material exceeds a predetermined threshold value, the switching magnetic field $H_{SW}$, its magnetic polarization undergoes a rapid reversal. This reversal of magnetisation generates a magnetic pulse with intense harmonic components.

The tracer 7 comprises a liquid comprising a plurality of magnetic nanoparticles. For example, the tracer 7 may comprise a plurality of iron oxide nanoparticles. The nanoparticles may be described as superparamagnetic nanoparticles. When the tracer 7 is exposed to an external field the magnetic response may be substantially linear, that is, the magnetisation of the tracer 7 is directly proportional to the applied field. The magnetic response of the tracer 7 may be substantially linear when a strength of the external field is within a certain range. When the strength of the external magnetic field is higher than a certain linear threshold, the magnetisation of the tracer 7 may saturate, leading to a non-linear magnetic response.

The probe 10 of the detection system further contains one or more sense coils arranged to detect the changes in the magnetic field caused by the change in magnetisation of the marker 6 and/or tracer 7.

To detect a marker 6 in a typical lesion or site of interest the probe 10 must have a detection depth of at least 30 mm, preferably more than 40 mm and more preferably more than 50 mm. Ideally the marker 6 gives the same magnitude of response regardless of the direction in which the marker 6 is approached. This is to provide consistent feedback to a surgeon on the location of the marker 6 relative to the probe 10.

Figure 4:
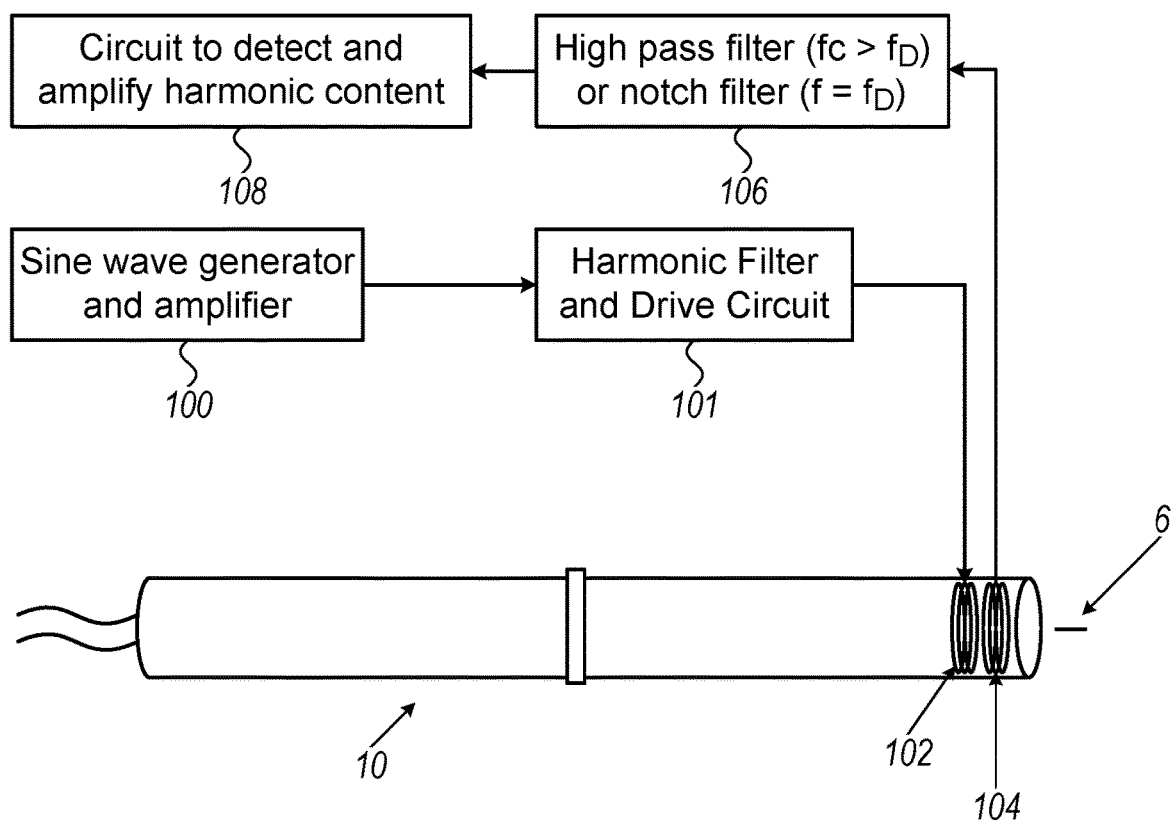
FIG. 4 is a schematic diagram of a magnetic detection system according to an embodiment.

FIG. 4 illustrates an example probe 10 in more detail. The detection probe 10 comprises a drive coil 102 to generate a driving magnetic field and a sense coil to detect a response magnetic field.

The drive coil 102 is configured to generate the driving magnetic field by means of an applied electrical current, comprising a driving signal. The driving magnetic field is an alternating magnetic field generated to alternate with a fundamental frequency component $f_1$. The driving magnetic field may further comprise one or more additional frequency components $f_n$. One or more of the additional frequency components $f_n$ may be spurious or unintended frequency components. Some or all of the additional frequency components $f_n$ may be harmonic frequencies of the fundamental frequency $f_1$.

The base unit 4 and probe 10 may further comprise a sine wave generator and amplifier 100 and a harmonic filter and drive circuit 101, configured to generate the driving signal at the fundamental frequency $f_1$. The sine wave generator and amplifier 100 is configured to generate and amplify an alternating current driving signal configured to alternate at the fundamental frequency $f_1$. The driving signal may be generated with one or more spurious frequency components $f_n$. Additional frequency components may be introduced by amplification of the driving signal. The harmonic filter and drive circuit 101 is configured to filter the driving signal and provide the driving signal to the drive coil 102. The harmonic filter is configured to reduce the one or more additional frequency components $f_n$ in the driving signal. The harmonic filter may be a notch filter tuned to a specific harmonic. The filtered driving signal is provided to the drive coil 102 to generate the driving field.

The base unit may further comprise one or more processing units, for example, a microcontroller and/or a Field Programmable Gate Array (FPGA). The base unit may further comprise a memory unit, an analogue to digital converter (ADC), and a digital to analogue converter (DAC). The memory unit may be, for example, formed of SD RAM or any suitable volatile or nonvolatile storage. The microcontroller may further control and interact with a computer memory. The microcontroller may be, for example, a STM32F769 microcontroller from STM Electronics, or any other suitable microcontroller. The microcontroller and FPGA may generate the sine wave drive signal which is then converted to an analogue signal by the DAC before being amplified, for example using an operational amplifier.

The sense coil 104 is configured to generate an electrical sensed signal in response to a varying external magnetic field. The sense coil 104 is arranged to detect a response magnetic field generated by a magnetic material in response to the driving magnetic field. In particular, the sense coil 104 is arranged to detect a response magnetic field generated by the marker 6 and/or the tracer 7.

The detection probe 10 further comprises an electronic filter, e.g. a notch filter, 106 and a circuit to detect and amplify harmonic content 108. The electronic filter 106 may be configured to reduce or remove the fundamental frequency $f_1$ from the sensed signal, to improve the sensing of other frequency components $f_n$. The circuit to detect and amplify harmonic content 108 may further amplify one or more of the additional frequency components $f_n$, e.g., corresponding to one or more harmonic frequencies of the fundamental frequency $f_1$. The circuit may also suppress some unwanted frequency components. The operation of the components for processing the sensed signal will be described in more detail below.

FIG. 5A shows a possible magnetisation curve for the magnetic marker 6. The curve shows the level of magnetisation of the marker 6 in relation to the strength of an applied external magnetic field. The marker 6 may comprise at least one piece of a large Barkhausen jump material (LBJ). As described above, the LBJ material may produce a non-linear magnetisation curve. According to the magnetisation curve, an excitation field, H, lower than the switching field 25 will result in little or no change to the magnetisation, B, except the effect of moving from '24' to '25', a small change in magnitude, but no change in polarity of B. The curve shows a reversal of magnetisation once the switching field indicated by '25' is exceeded. The curve shows a hysteresis effect, with a further reversal of magnetisation once the switching field indicated by '30' is exceeded. In this way, the reversal occurs regularly in time with the same time period as the driving frequency.

FIG. 5B shows a typical sensed signal corresponding to the magnetisation curve of FIG. 5A. When the marker 6 is excited by an alternating field with a sufficiently high amplitude, pulses corresponding to the reversal of magnetisation are seen in the time domain. The pulses may be superimposed onto a sine wave, if a spurious drive magnetic field coupled into the sense coils is not being filtered out fully. As will be discussed in more detail below, a material having a linear magnetic response would produce a sinusoidal sensed signal at the same frequency as the driving magnetic field. In comparison, the non-linear response of the marker 6 produces many harmonic frequency components in the sensed signal, which combine in superposition to produce the resulting pulse signal.

FIG. 5C illustrates the sensed signal corresponding to the magnetisation curve of FIG. 5A in the frequency domain. In response to the drive magnetic field substantially at the fundamental frequency ($f_1$), the sensed signal comprises at least one additional frequency component at a higher harmonic frequency. As shown, the sensed signal may comprise a significant component in each of at least the 2nd to 10th harmonic frequencies ($f_2$-$f_{10}$) with respect to the fundamental frequency. Higher frequency components may also be present.

The marker 6 may be configured to provide a significant response at a specific harmonic frequency ($f_x$). Such harmonic frequency $f_x$ may be utilised to distinguish between a portion of the sensed signal generated by the marker 6 and another portion generated by one or more secondary magnetic sources. The harmonic frequency $f_x$ may be utilised to distinguish between the marker 6 and the tracer 7. In some implementations, the third harmonic frequency ($f_3$) may be utilised to distinguish between the marker 6 and the tracer 7.

In the response magnetic field generated by the marker 6, a ratio between a fundamental frequency response and a particular harmonic frequency $f_x$ may be referred to as a marker response factor, or primary response factor. The marker response factor may be approximately 100 or may be less than 100. In some implementations, the marker response factor may be less than 50, for example, the marked response factor may be approximately 30 before any filter is applied.

Instead of operating in bistable mode, the non-linear marker may operate in a sub-bistable mode. As described above, some LBJ materials can still exhibit a non-linear response at fields smaller than the switching field (e.g. the third harmonic H3 response) that is almost 2 orders of magnitude larger than non-LBJ materials. This can allow the detection of a marker which is further away from the probe 10, where drive fields are typically small.

Figure 6A:
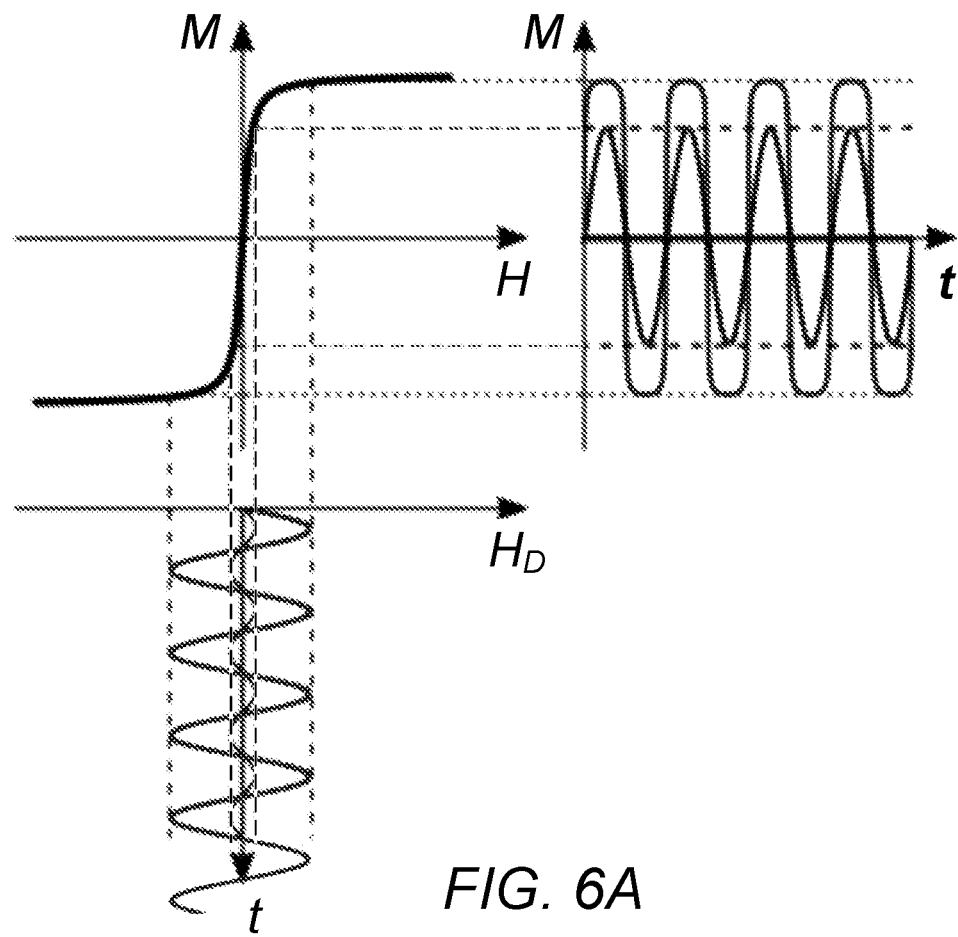
FIG. 6A is a chart showing a magnetisation curve for an exemplary tracer.

FIG. 6A shows a typical magnetisation curve for the magnetic tracer 7. The curve shows the level of magnetisation of the tracer 7 in relation to the strength of an applied external magnetic field. The magnetic response of the tracer 7 is substantially linear at low excitation fields. In higher external magnetic fields the magnetisation of tracer 7 may saturate, as the nanoparticles in the tracer 7 fully align with the external magnetic field. The magnetic response of the tracer 7 is linear in a low excitation field, and may become non-linear in response to a higher excitation field. According to the magnetisation curve, a sinusoidal excitation field, H, having an amplitude lower than a certain linear threshold will result in a corresponding sinusoidal magnetisation, M. An excitation field having an amplitude higher than the linear threshold may produce distortions in the corresponding magnetisation, i.e. a non-linearity. In addition, if a central part of the magnetisation curve is not linear (i.e. having a constant gradient), then further non-linear distortions in the corresponding magnetisation may be produced.

Figure 6B:
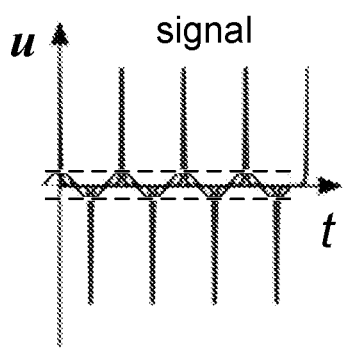
FIG. 6B is a chart showing a magnetic response in the time domain.

FIG. 6B shows a typical sensed signal corresponding to the magnetisation curve of FIG. 6A. When the tracer 7 is excited by an alternating field with an amplitude lower than the linear threshold, the sensed signal corresponds linearly to the excitation field. Where the alternating field has a sinusoidal form, the sensed signal has a corresponding sinusoidal form. When the tracer 7 is excited by an alternating field with a sufficiently high amplitude, pulses corresponding to the saturation of the tracer 7 magnetisation may be seen in the time domain. The non-linear response produces one or more harmonic frequency components in the sensed signal, which combine in superposition to produce the resulting pulse signal.

Figure 6C:
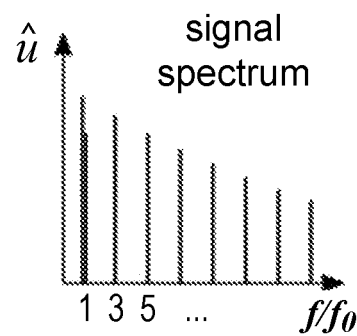
FIG. 6C is a chart showing a magnetic response in the frequency domain.

FIG. 6C illustrates the sensed signal corresponding to the magnetisation curve of FIG. 6A in the frequency domain. As can be seen, in response to the low-amplitude drive magnetic field substantially at the fundamental frequency ($f_1$), the sensed signal comprises primarily the fundamental frequency ($f_1$). In response to the high-amplitude drive magnetic field substantially at the fundamental frequency ($f_1$), the sensed signal comprises at least one additional frequency component at a higher harmonic frequency. As shown, the sensed signal may comprise a significant component in any of at least the 2nd to 10th harmonic frequencies ($f_2$-$f_{10}$) with respect to the fundamental frequency. In particular, there may be a significant component in the odd harmonic frequencies and the third harmonic in particular. Higher frequency components may also be present.

Harmonic frequency components in the sensed signal generated by the tracer 7 can interfere with the detection of harmonic frequency components generated by the marker 6, and can impede accurate detection of the marker 6.

As described above, the marker 6 may be configured to provide a significant response in a harmonic frequency $f_x$. The harmonic frequency $f_x$ may be utilised to distinguish between the portion of the sensed signal generated by the marker 6 and the portion generated by one or more secondary magnetic sources. However, generation of a sensed signal component at the harmonic frequency $f_x$ by the tracer 7 may inhibit accurate detection of the marker 6. Generating a driving magnetic field with an amplitude below a linear threshold for the tracer 7 can reduce the generation of harmonic frequency components by the tracer 7. In particular, using a low amplitude driving magnetic field can reduce the generation of third harmonic frequency components by the tracer 7.

In the response magnetic field generated by the tracer 7, a ratio between a fundamental frequency response and third harmonic frequency may be referred to as a secondary response factor.

Figure 7:
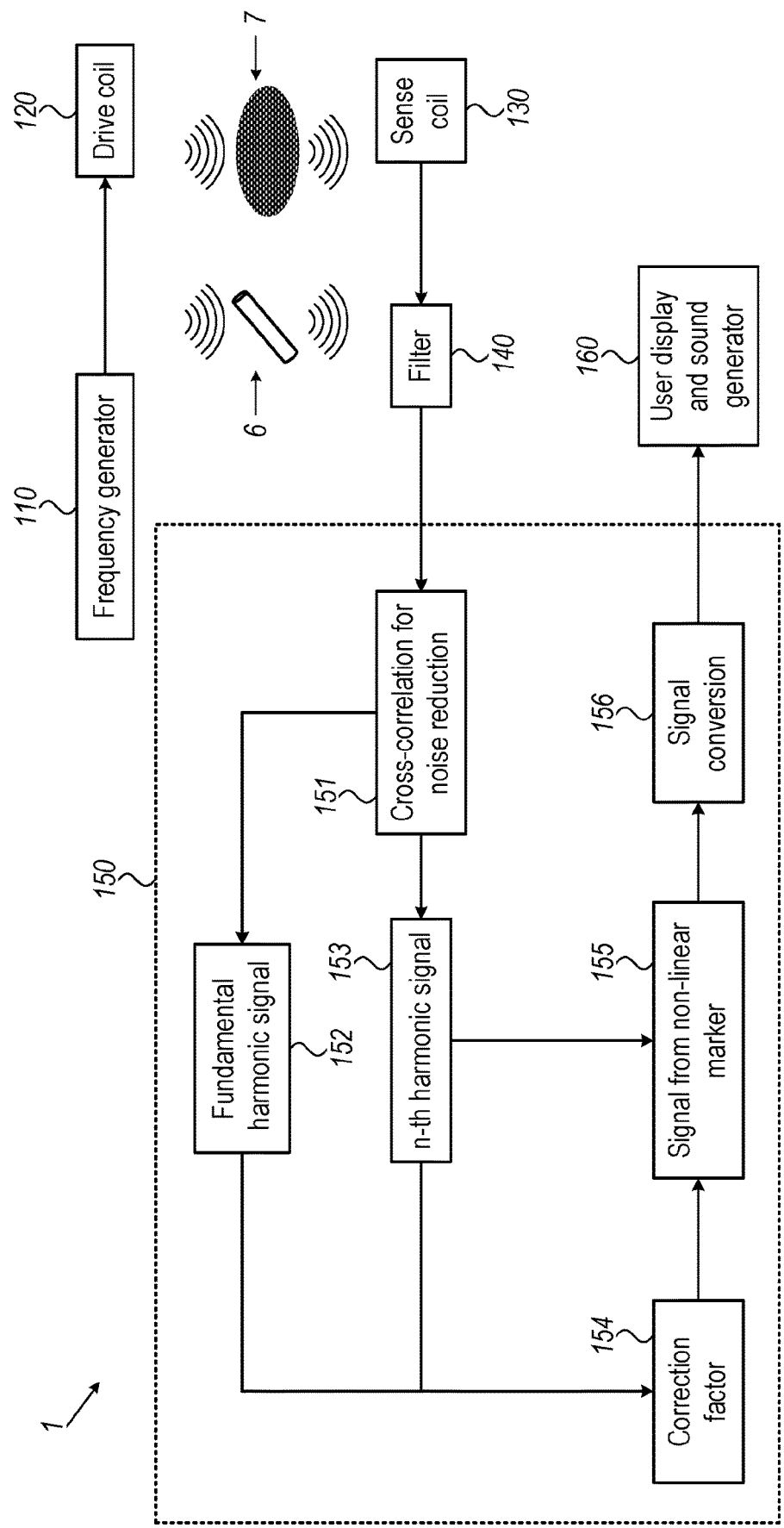
FIG. 7 is a schematic diagram of a magnetic detection system according to an embodiment.

FIG. 7 shows a block diagram of a magnetic detection system 1 according to an embodiment of the present invention. The magnetic detection system 1 comprises a frequency generator 110. An oscillator or a waveform generator is an example of a frequency generator 110. The frequency generator 110 is configured to generate an alternating signal. The signal may be sinusoidal. A frequency fp of the signal may be in a range of 100 Hz to 100 kHz. An example of frequency generator is a microcontroller outputting a sine wave that is then converted to an analog signal by a digital to analog converter and filtered by a low pass filter to smooth the signal.

The generated signal excites one or more drive coils 120. The one or more drive coils generate an alternating magnetic field. The generated field extends into the tissue containing a magnetic marker 6 comprising at least one piece of a large Barkhausen jump material (LBJ). A sinusoidal signal can minimise the harmonic components in the alternating magnetic field, however, the alternating signal and/or the generated alternating magnetic field may comprise one or more spurious higher frequency components. The alternating magnetic field may comprise one or more harmonic components. A ratio between a fundamental frequency and the harmonic frequency $f_x$ in the generated alternating magnetic field may be referred to as a driving factor.

The drive signal generated by the frequency generator 110 may be electronically filtered to attenuate any harmonic parts of the drive signal so that the alternating magnetic field is primarily at the desired excitation or drive frequency. This helps to avoid spurious responses at higher frequencies that could be erroneously interpreted as harmonic responses. Filtering and processing of the drive signal may significantly reduce the harmonic frequency $f_x$ component by several orders of magnitude. The harmonic frequency $f_x$ may be a factor of $10^3$ or $10^4$ smaller than the fundamental frequency component. That is, the value of the driving factor may be in the range of $10^3$ to $10^4$, or higher. However, even such a small component at the harmonic frequency $f_x$ may impede the accurate detection of the marker 6.

The alternating magnetic field excites the marker 6 and the magnetisation of the marker 6 leads to the generation of harmonic components in the response field. Depending on the arrangement of the marker 6, the harmonics may be odd harmonics, (3rd, 5th, 7th etc.) or even harmonics (2nd, 4th, 6th etc.) or a combination of both odd and even harmonics. The marker 6 can be detected by measuring the magnitude of one or more of the harmonic frequencies directly or by measuring the ratio of the magnitude of one or more harmonics to others or to the magnitude of the fundamental frequency.

The alternating magnetic field can also excite the tracer 7. The tracer distribution in space is normally unknown. However, if the amplitude of the alternating magnetic field is below the linear threshold for any of the tracer 7 in the volume surrounding the probe 10 then a magnetic response of the tracer 7 is linear, independent of the distribution of the tracer in space. The magnetisation of the tracer leads to the generation of a response field with a large fundamental frequency component, in response to the large fundamental frequency component of the driving magnetic field. In addition, the linear response of the tracer 7 may lead to one or more higher frequency components in response to the spurious higher frequency components in the driving magnetic field. Thus, the response field generated by the tracer 7 may include one or more harmonic frequency components, due to the harmonic frequency components in the driving magnetic field.

The response field from the marker 6 and the tracer 7 is detected by one or more sense coils 130 to generate a sense voltage or current. The sense coils 130 may be arranged in a handheld or robotic probe, such as the probe 10. An electronic filter 140 may be arranged to filter out or attenuate at least components of the sense signal at the drive frequency so that the resulting signal has minimal content at the drive frequency and comprises higher harmonic components of the signal, for example the second, third, fourth, fifth or seventh order harmonics or combinations of these. The filter 140 may take the form of a passive LCR type filter comprising a known arrangement of for example capacitors, inductors and resistors or an active filter comprising a known arrangement for example based on one or more op-amps.

The filtered signal may be fed to a harmonic detection circuit 150 which improves the signal to noise ratio of one or more harmonic components of the signal and converts the signal to a measure of distance from the probe 10 to the marker 6. The harmonic detection circuit 150 may be configured to filter a spurious harmonic response generated by the tracer 7. The harmonic detection circuit 150 may perform a number of operational steps. The functions of the harmonic detection circuit 150 may be performed by a microcontroller and FPGA, as described above.

The harmonic detection circuit 150 may be configured to perform cross-correlation for noise reduction 151. The harmonic detection circuit 150 may be configured to separate the signal into a plurality of frequency components by cross-correlation 151. For example, the cross correlation 151 may separate the signal into a fundamental harmonic signal 152 and at least one n-th harmonic signal 153.

The harmonic detection circuit 150 may determine a correction factor 154. The correction factor 154 may correspond to a sensed signal that is generated by the tracer 7. The correction factor 154 may correspond to a chosen n-th harmonic frequency component generated by the tracer 7. By removing the correction factor 154 from the n-th harmonic signal 153, the harmonic detection circuit 150 can isolate a signal from the non-linear marker 155. In particular, the harmonic detection circuit 150 can isolate the n-th frequency signal generated by the marker 6.

The correction factor 154 may be determined based on the fundamental harmonic signal 152. The correction factor 154 may be further based on the driving factor, representing the ratio of the fundamental frequency and the n-th harmonic frequency component in the driving magnetic field. In some implementations, the correction factor 154 may be further based on the characteristic spectral response of the linear tracer and the non-linear marker. The harmonic detection circuit 150 may reduce the fundamental harmonic signal 152 by the driving factor to determine the correction factor 154. This is a practical approximation that is particularly valid as long as the tracer is about 10 times more linear than the marker. This linearity can be evaluated by means of the corresponding harmonic distortion.

The correction factor 154, corresponding to the n-th harmonic frequency component generated by the tracer 7, may be expressed in terms of the fundamental frequency component generated by the tracer 7, using the secondary response factor described above. Furthermore, the fundamental frequency component generated by the tracer 7 and the fundamental frequency component generated by the marker 6 together make up the whole fundamental harmonic signal 152. A part of the n-th harmonic frequency component generated by the tracer 7 can therefore be related to the fundamental harmonic signal 152 based on the secondary response factor. A further part of the n-th harmonic frequency component generated by the tracer 7 can be related to the n-th harmonic frequency component generated by the marker 6, based on the secondary response factor and the marker response factor.

To the extent that the magnetic response of the tracer 7 is linear, the secondary response factor is substantially the same as the driving factor irrespective of the spatial variation of the drive field and of the spatial distribution of the tracer around the probe 10. That is, the value of the secondary response factor may be in the range of $10^3$ to $10^4$, or higher. It can be determined that the part of the n-th harmonic frequency component generated by the tracer 7 that is based on the secondary response factor and marker response factor is negligible, due to the large disparity between the secondary response factor and the marker response factor.

As a result, the correction factor 154 may be determined to a high degree of accuracy based only on the fundamental harmonic signal 152 and the driving factor of the driving signal.

The harmonic detection circuit 150 may be configured to remove the correction factor 154 from the n-th harmonic signal 153 to isolate a signal from the non-linear marker 155. The signal from the non-linear marker 155 may be referred to as a detection signal. A similar methodology can be applied to reject spurious signals arising from different sources, other than the tracer 7. For example, a linear signal could come from metal objects that are in the proximity of the probe 10 during surgery, from the patient's body, from the surgeon's hands or from a biopsy marker. The harmonic detection circuit 150 may reject any such signals that are small enough that they don't saturate electronic components in the sense circuits.

In some embodiments the frequency generator 110 may be configured to vary an amplitude of the driving signal over time. The amplitude of the alternating magnetic field generated by the drive coils 120 may be varied over time. In this way it is possible to magnetically excite different portions of volume around the probe 10 at different times. The harmonic detection circuit 150 may be configured to calculate a plurality of correction factors 154 at different times, corresponding to different amplitudes of the driving signal. The calculated plurality of correction factors 154 may be arranged in an array of correction factors. The signal from the non-linear marker 155 may be isolated based on the array of correction factors. In this way, the system can more accurately reject spurious signals from a secondary source that is unevenly distributed around the probe 10.

The harmonic detection circuit 150 may be further configured to perform signal conversion 156 on the n-th harmonic marker signal 155 to generate a measure of distance from the probe 10 to the marker 6. A user display and sound generator 160 provides a visual and audio output to the user indicating for example, the proximity of the marker 6 or the magnitude of the magnetic signal. The system may indicate the proximity, size, distance/direction or orientation of the marker 6, or combinations of these.

By generating a correction factor corresponding to the nth harmonic frequency component generated by the tracer 7, and isolating the n-th harmonic frequency component generated by the marker 6, the magnetic detection system 1 can provide a significantly improved indication of the proximity, size etc. of the marker 6. The magnetic detection system 1 can accurately distinguish between the marker 6 and tracer 7, even when the drive signal does not have a pure single-frequency sinusoidal waveform. The magnetic detection system 1 may improve the accuracy of localising a marker 6, and allow for a more accurate removal of a corresponding lesion. The magnetic detection system 1 may thus reduce the occurrence of excess tissue removal, by allowing a surgeon to more accurately determine the extent of a lesion, thus improving recovery time and a better surgical outcome.

In other cases, the magnetic detection system 1 may provide a more accurate indication of the size or quantity of a magnetic marker, where the magnetic marker may correspond to a sample of any material providing a non-linear magnetic response. The magnetic detection system 1 may improve the determination of size or quantity, even when the drive signal includes a spurious frequency component in addition to the desired fundamental frequency component.

In addition, extracting the n-th harmonic frequency component generated by the marker 6, together with knowledge of its spectral response, is equivalent to extracting the harmonic frequency components generated by the tracer 7. This may be used to quantify the amount of tracer 7 in the proximity of the probe 10, or a distance of the tracer 7 from the probe 10, even in the presence of a marker 6 that produces both an n-th harmonic frequency and a fundamental harmonic frequency component.

The markers of the detection system described above may each comprise one or more lengths of material ("magnetic marker material") which gives a harmonic or non-linear response to an alternating magnetic field produced by a large Barkhausen discontinuity in the magnetisation curve. Examples of such materials include iron-, cobalt- and nickel-rich glass-coated amorphous microwires, iron-silicon-boron based amorphous microwires, iron-cobalt based amorphous microwires, and bulk metallic glass wires.

In some embodiments, the length or lengths of magnetic marker material (formed from a material with a large Barkhausen discontinuity in its magnetisation curve) may comprise a length of solid wire (<10 mm long) with a diameter <2 mm so that the marker can be delivered through a small needle; a glass-coated microwire with core diameter between, e.g., 5 and 100 micrometres and a coating thickness of between, e.g., 0.5 and 40 micrometres; a bundle of 2 or more lengths of solid wire or glass-coated microwire; or a hollow tube.

Any of the markers may comprise more than one piece of magnetic marker material together with additional material to join or enclose the pieces of magnetic marker material and form the final shape of the marker. The marker may comprise a tube, tubes or a complete or partial shell of another material within which the lengths of magnetic material of the marker are held. The marker may comprise electronic components e.g. coils, diodes and transistors, for example an LC circuit (a combination of a capacitor and an inductor) with a diode can produce a non-linear response. The magnetic material may also be coated or enclosed within a further biocompatible material. For example, the tube or shell containing the magnetic marker material comprises a biocompatible plastically deformable material such as a 316 stainless steel, Titanium, Nitinol, Titanium alloy or similar.

In some embodiments, the drive unit may comprise one or more drive coils. Alternatively, an alternating magnetic field may be generated by, for example, a spinning permanent magnet. The sensing unit may comprise one or more sense coils or, alternatively, a solid state magnetometer. In some implementations, the sense unit may comprise any suitable magnetic sensor, e.g., a Hall effect sensor, mems sensor, magneto-transistor/magneto-diode, a SQUID magnetometer, AMR sensor, or a GMR sensor.

The drive frequency may be in the range 100 Hz to 100 kHz. Higher frequencies towards 100 kHz may be advantageous to maximise the sensed signal. A higher frequency may also allow more cycles per second to be averaged during detection to improve noise suppression while still delivering a 'real time' output to the user i.e. updating the output signal at least 10 times per second. Hence for noise suppression a frequency of at least 1000 Hz and preferably at least 10 kHz may be desirable. For example, in order to give an apparent 'real time' response to the user, the output may need to update at least every 0.1 s. A frequency of 1 kHz allows 100 cycles to be averaged between each update to the user, and 10 kHz allows 1000 cycles to be averaged between each update to the user.

Advantages may also be gained from a lower drive frequency, and these include reduced eddy current losses both in the marker (in cases where it is prone to eddy currents for example if it has high conductivity) and from the surrounding tissue and more intense magnetic switching in the marker. For reduced eddy current losses, a frequency of less than 50 kHz and preferably less than 30 kHz may be advantageous. In the operating room environment, electromagnetic interference signals may be more frequently experienced at frequencies above 100 kHz and therefore choosing a drive frequency such that the harmonics of interest are less than 100 kHz may be beneficial.

Figure 8:
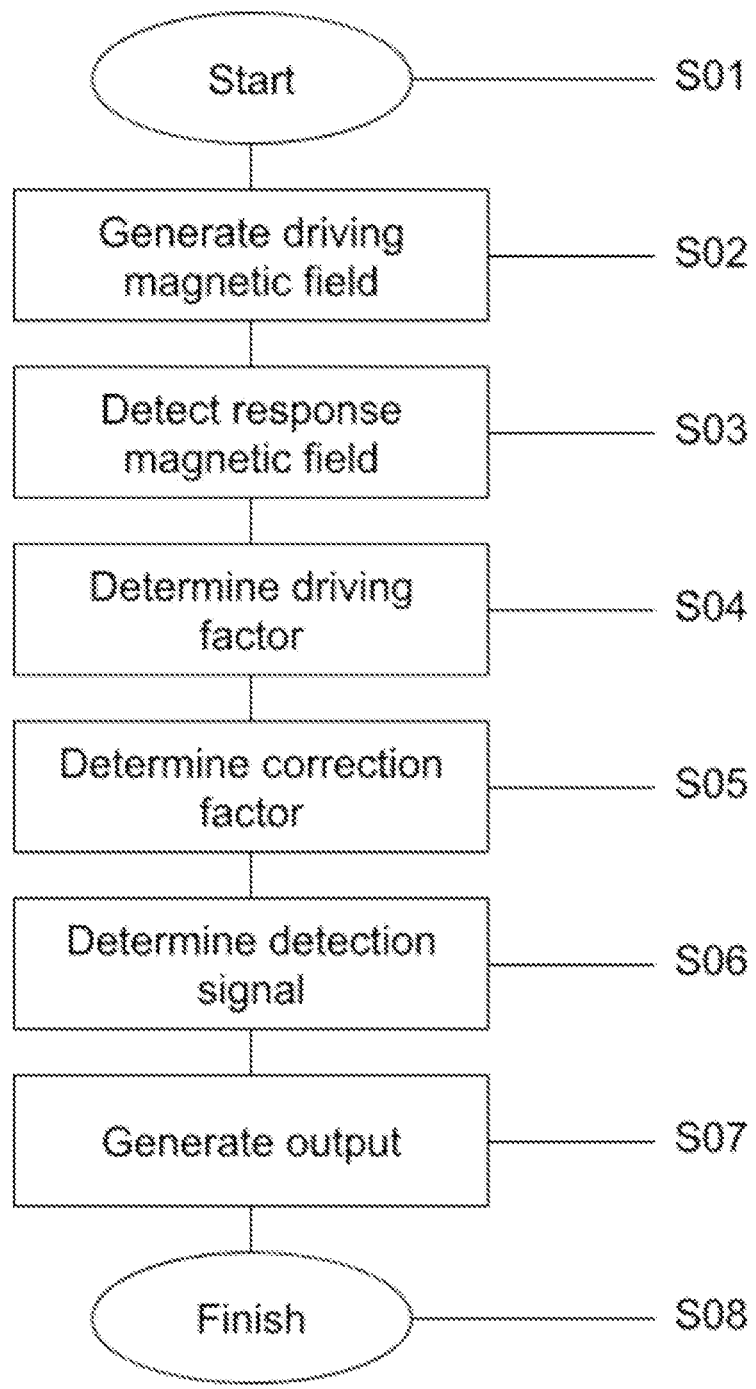
FIG. 8 is a flowchart showing a method according to an embodiment.

FIG. 8 of the accompanying drawings shows a flowchart representing a method of detecting a magnetic marker according to an embodiment. The method starts at step S01.

At step S02, a driving magnetic field is generated. The driving magnetic field is generated with a driving unit. The driving magnetic field comprises a first driving component ($DH_1$) at a first frequency and a second driving component ($DH_n$) at a second frequency. The first frequency may be a first fundamental frequency and the second frequency may be an $n^{th}$ harmonic of the first frequency.

At step S03, a response magnetic field is detected. The response magnetic field is detected with a magnetic field sensor. The response magnetic field comprises a first response component ($SH_1$) at the first frequency and a second response component ($SH_n$) at the second frequency. $SH_1$ includes two sub-components: a marker sub-component ($MH_1$) and a secondary sub-component ($TH_1$). $SH_n$ also includes two sub-components: a marker sub-component ($MH_n$) and a secondary sub-component ($TH_n$).

The marker sub-components may be referred to as primary sub-components or primary portions. The secondary sub-components (or secondary portions) may come from a magnetic tracer or other source of magnetic signal. $MH_n$ is a desired signal from the marker and $TH_n$ is an unwanted interfering signal from the tracer or other secondary source.

At step S04, a driving factor $DF=DH_1/DH_n$ is generated. The driving factor represents a ratio of the first driving component and the second driving component in the driving signal. The driving factor is generated by a processor.

At step S05, a correction factor to compensate for $TH_n$ is determined. That is, the correction factor corresponds to the secondary subcomponent of $SH_n$. The correction factor is determined by the processor. The correction factor is determined based on the first response component ($SH_1$) and the driving factor (DF).

At step S06, a detection signal corresponding to the marker sub-component of the second response component is determined. The detection signal is determined by the processor. The detection signal is determined based on the second response component ($SH_n$) and the determined correction factor.

At step S07, an output signal is generated. The output signal is generated by the processor for output. The output signal is based on a strength of the detection signal.

The method finishes step S08.

Although aspects of the invention herein have been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the scope of the invention as defined by the appended claims.

The invention claimed is:

1. A method for detecting a magnetic marker, comprising:
generating, by a driving unit, a driving magnetic field, comprising a first driving component at a first frequency and a second driving component at a second frequency, the second frequency being an n-th harmonic of the first frequency;
detecting, by a magnetic field sensor, a response magnetic field comprising a first response component at the first frequency and a second response component at the second frequency,
wherein a primary portion of the first response component and a primary portion of the second response component are generated by the magnetic marker in response to the driving magnetic field; the magnetic marker having a non-linear response to the driving signal, and
wherein a secondary portion of the first response component and a secondary portion of the second response component are generated by at least one secondary magnetic source in response to the driving magnetic field; the secondary magnetic source having a linear response to the driving magnetic field;
determining, by a processor, a driving factor representing a ratio of the first driving component and the second driving component in the driving signal; the driving factor being approximately equal to a ratio of the secondary portion of the first response component and the secondary portion of the second response component;
determining, by the processor, from the first response component and the driving factor, a correction factor corresponding to the secondary portion of the second response component;
determining, by the processor, a first detection signal corresponding to the primary portion of the second response component, wherein the first detection signal is determined from the second response component and the correction factor; and
generating, by the processor, first output signal based on a strength of the first detection signal.

2. The method of claim 1, wherein the magnetic marker is formed from a material showing a Large Barkhausen Jump (LBJ) in its magnetisation curve.

3. The method of claim 1, wherein the magnetic marker is configured to exhibit bistable behaviour in response to a sinusoidal driving signal, oscillating between two magnetic polarisation states.

4. The method of claim 1, wherein the driving signal is generated with an amplitude below a threshold amplitude level, above which a response of the secondary magnetic source to the driving signal becomes non-linear.

5. The method of claim 1, wherein a primary response factor representing a ratio between the primary portion of the first response component and the primary portion of the second response component is substantially smaller than a secondary response factor that corresponds to a ratio between a secondary portion of the first response component and a secondary portion of the second response component.

6. The method of claim 5, wherein the magnetic marker is formed from a magnetically responsive material configured to provide the marker response factor with a value substantially less than 300.

7. The method of claim 1, wherein determining the correction factor is further based on the second response component, a spectral response of the secondary magnetic source and a spectral response of the marker.

8. The method of claim 7, wherein the secondary magnetic source comprises a plurality of superparamagnetic iron oxide nanoparticles.

9. The method of claim 1, wherein the secondary magnetic source is formed from a paramagnetic material.

10. The method of claim 1, wherein the second frequency is a third order harmonic frequency of the first frequency.

11. The method of claim 1, further comprising:
determining, by the processor, a secondary detection signal that is different from the first detection signal based on the secondary portion of the first response component and the secondary portion of the second response component; and
generating, by the processor for output, a secondary output signal that is different from the first output signal based on a strength of the secondary detection signal.

12. The method of claim 11, wherein an amplitude of the secondary output signal relates to an amount of magnetic material of the magnetic marker or the secondary magnetic source.

13. The method of claim 11, wherein the secondary detection signal corresponds to the secondary magnetic source.

14. The method of claim 1, wherein the secondary magnetic source is any one of a surgical tool, a biopsy marker or a human body.

15. The method of claim 1, wherein an amplitude of the first output signal relates to a proximity of the magnetic marker to the magnetic field sensor.

16. The method of claim 1, further comprising:
varying, by the driving unit, an amplitude of the driving magnetic field over time, and
determining, by the processor, a plurality of additional correction factors based on respective plurality of driving magnetic field amplitudes and generating an array of correction factors, and
wherein the detection signal is determined based on the second response component and the generated array of correction factors.

17. The method of claim 1, wherein the driving factor is in the range of approximately $10^3$ to $10^4$ or higher.

18. A detection system for detecting a magnetic marker, comprising:
a driving unit configured to generate a driving magnetic field, comprising a first driving component at a first frequency and a second driving component at a second frequency;
a magnetic field sensor configured to detect a response magnetic field, comprising a first response component at the first frequency and a second response component at the second frequency, the second frequency being an n-th harmonic of the first frequency,
wherein a primary portion of the first response component and a primary portion of the second response component are generated by the magnetic marker in response to the driving magnetic field; the magnetic marker having a non-linear response to the driving signal; and
wherein a secondary portion of the first response component and a secondary portion of the second response component are generated by at least one secondary magnetic source in response to the driving magnetic field; the secondary magnetic source is configured having a linear response to the driving magnetic field; and
a processor configured to:
determine a driving factor representing a ratio of the first driving component and the second driving component in the driving signal; the driving factor being approximately equal to a ratio of the secondary portion of the first response component and the secondary portion of the second response component;
determine, from the first response component and the driving factor, a correction factor corresponding to the secondary portion of the second response component, wherein the correction factor is determined based on the first response component and the driving factor;
determine a first detection signal corresponding to the primary portion of the second response component, wherein the detection signal is determined from the second response component and the correction factor; and
generate, first output signal to a user-based on a strength of the first detection signal.

19. The method of claim 18, wherein the driving factor is in the range of approximately $10^3$ to $10^4$ or higher.

* * * * *